United States Patent [19]
Ashley

[11] Patent Number: 5,792,446
[45] Date of Patent: Aug. 11, 1998

[54] DELIVERY SYSTEM FOR ADMINISTERING DENTIN-HYPERSENSITIVITY-AMELIORATING COMPOSITIONS

[75] Inventor: Robert A. Ashley, Newtown, Pa.

[73] Assignee: Collagenex Pharmaceuticals, Inc., Newton, Pa.

[21] Appl. No.: 802,316

[22] Filed: Feb. 18, 1997

[51] Int. Cl.$^6$ ..................... A61K 7/18
[52] U.S. Cl. ..................... 424/52
[58] Field of Search ..................... 424/52, 434

[56] References Cited

U.S. PATENT DOCUMENTS

| | | |
|---|---|---|
| 3,122,483 | 2/1964 | Rosenthal et al. |
| 3,847,155 | 11/1974 | Bernaola ..................... 128/334 |
| 4,003,971 | 1/1977 | Mannara ..................... 264/9 |
| 4,083,955 | 4/1978 | Grabenstetter et al. |
| 4,098,435 | 7/1978 | Weyn |
| 4,400,372 | 8/1983 | Muhler et al. ..................... 424/48 |
| 4,647,450 | 3/1987 | Peters et al. |
| 4,753,800 | 6/1988 | Mozda |
| 4,772,470 | 9/1988 | Inoue et al. ..................... 424/435 |
| 4,824,681 | 4/1989 | Schobel et al. |
| 4,847,090 | 7/1989 | Della Posta et al. |
| 4,853,212 | 8/1989 | Faust et al. |
| 4,867,989 | 9/1989 | Silva et al. |
| 4,879,108 | 11/1989 | Yang et al. |
| 4,929,447 | 5/1990 | Yang et al. |
| 4,933,172 | 6/1990 | Clark, Jr. et al. |
| 4,933,190 | 6/1990 | Cherukuri et al. |
| 4,971,806 | 11/1990 | Cherukuri et al. |
| 4,990,327 | 2/1991 | Neirinckx |
| 5,139,768 | 8/1992 | Friedman ..................... 424/45 |
| 5,403,577 | 4/1995 | Friedman ..................... 424/45 |
| 5,487,902 | 1/1996 | Andersen et al. ..................... 426/3 |
| 5,534,244 | 7/1996 | Tung ..................... 424/52 |

FOREIGN PATENT DOCUMENTS

| | | |
|---|---|---|
| 907514 | 8/1972 | Canada . |
| 1552119 | 9/1979 | United Kingdom . |

*Primary Examiner*—Peter F. Kulkosky
*Attorney, Agent, or Firm*—Hoffman & Baron, LLP

[57] ABSTRACT

A delivery system for controlled administration of a dentin-hypersensitivity-ameliorating composition to targeted areas is described. In particular, a bio-compatible delivery vehicle is described which contains unreacted, reactive materials dispersed therein. These materials form a dentin-hypersensitivity-ameliorating composition when reacted. Furthermore, these materials are separately encapsulated within protective encapsulating matrices to prevent the reaction thereof until delivery of the materials to a dentinal surface.

23 Claims, No Drawings

DELIVERY SYSTEM FOR ADMINISTERING DENTIN-HYPERSENSITIVITY-AMELIORATING COMPOSITIONS

BACKGROUND OF THE INVENTION

The present invention relates generally to the art of ameliorating dentin hypersensitivity, and, in particular, to new systems and methods for delivering dentin-hypersensitivity-ameliorating compositions to targeted areas.

Dentin hypersensitivity is a significant clinical problem which affects 8% to 30% of the adult population. The symptoms often cause patients to reject dental treatment. The sensitivity may be local or general and often complicates other pre-existing problems. It is believed that dentin hypersensitivity is caused by fluid movement within dentinal tubules which transmit various signals to free nerve endings of A-delta nerve fibers. These nerve fibers terminate near the odontoblastic layer or just into the pulpal end of the dentinal tubules. Thus, it is these nerve fibers that mediate the pain which is symptomatic of dentin hypersensitivity.

Treatment of dentin hypersensitivity has resulted in varying degrees of success. These treatments often have relied upon astringent or coagulating effects of various agents, occluding properties of various compositions, and the ability to render calcium less stable. Examples of these agents include fluoride, formaldehyde, silver nitrate, zinc oxide and strontium chloride.

Strontium chloride is known to be particularly effective in desensitizing dentin. To be effective, strontium chloride must penetrate the dentinal surface. Strontium chloride, however, is highly soluble in aqueous solutions. Accordingly, when a solution of strontium chloride is applied to the oral cavity, the strontium chloride exhibits a higher affinity for its aqueous environment than for dentinal surfaces.

Because fluoride is known to be effective in minimizing or preventing cavity formation in teeth, attempts have been made to combine physiologically acceptable sources of fluoride and strontium to fight cavities while treating dentin hypersensitivity. Such attempts have met with limited success because strontium and fluoride readily react to form a strontium fluoride precipitate. Precipitated strontium fluoride is too large to penetrate through the surface of the dentin. Accordingly, such preparations are ineffective in delivering the desired dentin desensitization.

Methods have been described for isolating one or both ionic species, i.e., strontium and fluoride, with various chelating agents to prevent premature precipitation of strontium fluoride prior to delivery to a dentinal surface. For example, Canadian Patent No. 907,514 to Stearns et al. describes a dental desensitizing composition which includes a source of fluoride and a chelated source of strontium which is chelated with, for example, ethylenediaminetetraacetic acid (EDTA). A composition containing EDTA-chelated strontium and fluoride effectively prevents precipitation of strontium fluoride prior to delivery to the oral cavity so that both strontium and fluoride ions are readily available at the dentinal surfaces. The ability of the chelated strontium to penetrate the surface of the dentin, however, is significantly decreased as compared to free strontium ions per se. Furthermore, when chelated, strontium is significantly less reactive with fluoride. Thus, the ability of a composition containing fluoride and chelated strontium to ameliorate dentin hypersensitivity is substantially decreased.

Alternatively, attempts have been made to mechanically isolate separate sources of strontium and fluoride until delivery to the oral cavity. When successful, it is known that simultaneous delivery of reactive forms of strontium and fluoride at a dentinal surface produces a synergistic effect. In particular, U.S. Pat. No. 4,990,327 to Neirinckx describes dental desensitizing compositions, such as toothpastes and mouthwashes, in which the sources of strontium and fluoride are separated, i.e., mechanically isolated, until delivery to the oral cavity. For example, the Neirinckx reference describes a single container having multiple compartments wherein strontium and fluoride phases are housed separately until they are dispensed. Alternatively, the Neirinckx reference describes housing sources of strontium and fluoride in two separate containers which are then dispensed and mixed prior to delivery to the oral cavity.

The Neirinckx system for delivering mechanically isolated sources of strontium and fluoride ions suffers from several drawbacks. First, because each source of strontium and fluoride is maintained independent of the other, the amount of each ionic species delivered to the oral cavity can vary widely. Accordingly, there is an inefficient delivery of strontium fluoride to the dentinal surfaces which results in decreased dentin desensitizing effects. Furthermore, once the sources of strontium and fluoride come into contact, they immediately react to form strontium fluoride for example, at the lip of the dispensing container, in the mixing container, or in the oral cavity prior to contact with the dentin surface. Accordingly, the amount of strontium fluoride which is able to penetrate into the dentin tubules is substantially diminished. Thus, the dentin desensitizing effect of such preparations is also significantly lowered.

Accordingly, it would be desirable to provide a system for delivering in substantially unreacted form components of a dentin-hypersensitivity-ameliorating composition to targeted areas, wherein these components react at the delivery site to form the dentin-hypersensitivity-ameliorating composition. It is also desirable to provide a delivery system wherein controlled quantities of strontium and fluoride sources are delivered to targeted areas for efficient reaction thereon. It would also be desirable to provide a system that prevents premature precipitation of strontium fluoride at the mouth of delivery devices and blockages thereof.

SUMMARY OF THE INVENTION

The present invention includes a method for preparing a delivery system for ameliorating dentin hypersensitivity and delivery systems for the adminstration of dentin-hypersensitivity-ameliorating compositions to targeted areas. One delivery system of the present invention includes a controlled administration of a dentin-hypersensitivity-ameliorating composition through a bio-compatible delivery vehicle containing at least first and second unreacted, reactive materials dispersed therein. These unreacted materials form a dentin-hypersensitivity-ameliorating composition when reacted, and are separately incorporated within protective matrices to prevent their reaction until delivery of these materials to a targeted area.

Another embodiment of the present invention is a system for simultaneously administrating to a targeted area protected precursors which react to form a dentin-hypersensitivity-ameliorating agent. This system includes a base and a matrix which is in intimate contact with the base. The matrix includes (1) protective bodies which incorporate at least a first ionic precursor of a pharmaceutically acceptable source of strontium compounds, (2) additional protective bodies which incorporate at least a second ionic precursor of a pharmaceutically acceptable source of fluoride compounds, (3) a plasticizer and (4) an optional outer coating of a hydrophilic polymer. The protective bodies of this embodiment maintain at least the first and second ionic precursors in an unreacted state until delivery to a targeted area, i.e., dentinal surfaces in the oral cavity.

The systems of the present invention include delivery vehicles or base materials which may include dissolvable tablets, confections, troches, chewing gums, toothpaste formulations, and comestibles, including mouthwashes. Furthermore, the reactive ingredients of the present invention described herein as "reactive materials" or "ionic precursors" may take different forms. One of the materials of the present invention which is referred to as the "first reactive material" or "ionic precursor" includes, for example, fluoride-containing compounds, such as for example, sodium fluoride, sodium monofluorophosphate, potassium fluoride, lithium fluoride, zinc fluoride, ammonium fluoride, rubidium fluoride, potassium bifluoride, ammonium bifluoride, sodium silicofluoride and mixtures thereof. Another of the materials of the present invention which is referred to as the "second reactive material" or "ionic precursor" includes, for example, strontium-containing compounds including strontium chloride, strontium nitrate, strontium acetate, strontium bromide, strontium iodide, strontium bromate, strontium perchlorate, strontium formate, strontium lactate and mixtures thereof. Preferably, the first reactive material or ionic precursor is sodium monofluorophosphate and the second reactive material or ionic precursor is strontium chloride.

These strontium- and fluoride- containing compounds are incorporated into protective bodies or matrices which include bio-compatible cellulose, cellulose derivatives, starches, carbohydrates, gums, polyolefins, polyesters, waxes, polymers, proteins, gelatin, zein, and mixtures thereof. The incorporated strontium- and fluoride- containing compounds are released, and form a dentin-hypersensitivity-ameliorating composition only at a dentinal surface in response to certain stimuli. These stimuli include for example, chewing, sucking, brushing, imbibing, pH change, temperature change and mixtures thereof.

An optional outer coating may be applied to the outer surface of the protective bodies for added protection against premature mechanical or chemical break down thereof. The outer coating is a hydrophilic polymer and may include, for example, gum arabic, gelatin, carrageenan, polyvinylpyrrolidone, cellulose methyl cellulose, ethyl cellulose, hydroxyethyl cellulose, hydroxypropyl cellulose carboxymethyl cellulose and mixtures thereof.

A further embodiment of the present invention includes a method of making a delivery system for ameliorating dentin hypersensitivity. This method includes preparing a dentin-hypersensitivity-ameliorating-agent delivery system wherein at least two reactive ionic species are chemically isolated, each from the others, by separately incorporating each into a protective matrix. The incorporation process includes entrapping a first ionic species in a mixture of polyvinyl acetate by melting and blending the first ionic species with polyvinyl acetate and a plasticizer to form a chemically discrete domain containing the first ionic precursor. This mixture is cooled to ambient temperature while continuing to mix. Then, the mixture is ground to a desired particle size and the particles are optionally coated with a hydrophilic hydrocolloid material. Second and subsequent ionic species is/are incorporated using the same process as described above. At least the first and second incorporated species are combined in controlled, pharmaceutically acceptable quantities to form the delivery system. The resultant delivery system is then combined with a biocompatible base for targeted delivery to dentin surfaces.

As a result of the present invention, sources of fluoride and strontium are prevented from reacting with each other to form strontium fluoride until delivery at, for example, dentinal surfaces. The delivery system allows for the controlled titration of specific amounts of each ionic species for efficient reaction and improved control over the delivery of strontium fluoride. Furthermore, the composition of the present invention is significantly easier to manipulate because the fluoride and strontium sources are chemically isolated in, for example, protective capsules so that both of these reactive ionic species can be co-located within a single delivery vehicle for ease of storage and dispensing.

These and other advantages will become apparent to the skilled artisan in view of the disclosure set forth herein.

DETAILED DESCRIPTION OF THE PREFERRED EMBODIMENTS

The present invention includes a delivery system for controlled administration of dentin-hypersensitivity-ameliorating (DHA) compositions to targeted areas. For purposes of the present invention, "dentin-hypersensitivity-ameliorating compositions" refers to those compounds which reduce or alleviate the symptoms caused by dentin hypersensitivity. Such compositions may include, for example, strontium containing compounds which are absorbed by dentinal surfaces and penetrate to reach the dentinal tubules. A preferred composition is strontium fluoride.

The present delivery system includes a bio-compatible delivery vehicle which contains therein at least two reactive materials which remain unreacted until delivery to a targeted area. For purposes of the present invention, the phrase "first and second reactive materials" refers to certain reactive ions contained in the reactive materials which when brought into contact with each preferentially react with each other to form a precipitate. This precipitate is effective in ameliorating dentin hypersensitivity only when it is formed in close proximity to dentinal surfaces. Thus, the first and second reactive materials must be chemically isolated in order to maintain the reactive ions in their non-reacted state until delivery onto a dentinal surface.

For purposes of the present invention, the terms "first reactive material" and "first ionic precursor" are used interchangeably to refer to certain pharmaceutically acceptable fluoride-containing compounds. Examples of such fluoride-containing compounds include sodium fluoride, sodium monofluorophosphate, potassium fluoride, lithium fluoride, zinc fluoride, ammonium fluoride, rubidium fluoride, potassium bifluoride, ammonium bifluoride, sodium silicofluoride and mixtures thereof. Preferably, the fluoride-containing compound is sodium monofluorophosphate.

In a similar fashion, the terms "second reactive material" and "second ionic precursor" are used interchangeably to refer to certain pharmaceutically acceptable strontium-containing compounds. Examples of such strontium-containing compounds include strontium chloride, strontium nitrate, strontium acetate, strontium bromide, strontium iodide, strontium bromate, strontium perchlorate, strontium formate, strontium lactate and mixtures thereof. Preferably, the strontium-containing compound is strontium chloride.

Although the present invention is described with reference to the preferred embodiment which includes first and second reactive materials, the skilled artisan will appreciate that any number of reactive materials may be used. Thus, the present invention is intended to include multiple reactive materials, i.e., more than two, which must be maintained in an unreacted condition until delivery to a targeted area.

For purposes of the present invention, any convenient bio-compatible delivery vehicle as known in the art may be used to deliver the reactive materials in an unreacted state to the oral cavity, and more particularly to dentinal surfaces therein. Such vehicles include, for example, dissolvable tablets, confections, troches, chewing gums, toothpaste formulations and comestibles, including mouthwashes. Comestibles include any compatible beverage or foodstuff which is retained in the oral cavity sufficiently long to release the active ingredients, i.e., the first and second reactive materials. In each of these, the first and second reactive materials are released from the vehicle in the course of chewing, sucking, brushing or imbibing and are allowed to pass over the dentinal surfaces. As described in further detail below, when the delivery vehicle is introduced into the oral cavity, changes in pH and temperature can also cause release of the reactive materials from the vehicle.

As stated hereinabove, certain ions contained in the unreacted first and second reactive materials form a DHA composition when reacted. This DHA composition is ineffective unless it is formed on or substantially near a dentin surface. To prevent premature formation of the DHA composition, the first and second reactive materials are separately incorporated within protective matrices.

For purposes of the present invention, "protective matrices" refer to materials which prevent the reaction of the first reactive material with the second reactive material until delivery to a dentinal surface. For example, the protective matrix may form a protective film on the first reactive material and the second reactive material, respectively. The protective film encapsulates each reactive material separately and prevents certain ions of the first and second reactive materials from reacting with each other until they are delivered to, for example, a dentinal surface. Alternatively, the protective matrices may include chelating agents or biological agents which incorporate the unreacted, reactive materials and only release them in response to certain stimuli in, for example, the oral cavity.

The protective matrices must be bio-compatible. These protective matrices may also be biodegradable, such as for example by degradation caused by natural enzymes present in the oral cavity. Alternatively, the protective matrices may be rupturable upon pressure supplied by the chewing or brushing of the teeth. Still further, the protective matrices may be dissolvable at physiologic temperatures or pH.

When released into the oral cavity on or in close proximity to the targeted dentinal surfaces, the first and second reactive materials dissociate and release, for example, controlled, pharmaceutically appropriate quantities of strontium and fluoride ions, respectively. These fluoride and strontium ions then react to form strontium fluoride at the dentinal surfaces. Not wishing to be bound by a particular theory, it is believed that the strontium fluoride formed at the dentinal surfaces is absorbed by the dentin and enters the dentinal tubules where it acts to ameliorate dentinal hypersensitivity.

The protective matrix which incorporates the first reactive material may be the same or different from the protective matrix which incorporates the second reactive material. The protective matrices of the present invention may include for example, cellulose, cellulose derivatives, starches, carbohydrates, gums, polyolefins, polyesters, waxes, polymers, gelatin, zein, proteins and mixtures thereof. Preferably, the protective matrices are a high molecular weight vinyl polymer. More preferably, the protective matrices are a high molecular weight polyvinyl acetate (PVA).

For purposes of the present invention, "high molecular weight polyvinyl acetate" refers to PVA having a molecular weight above 20,000 MWU as determined by gel permeation chromatography. High molecular weight PVA is a thermoplastic high polymer having a highly crystallin structure which is brittle. When combined with a hydrophobic plasticizer, however, the PVA forms a film that can be used to, for example, encapsulate the first and second reactive materials and prevent certain ions contained therein from reacting until delivery into the oral cavity. Thus, the first and second reactive materials can be dispersed or co-localized within a single delivery vehicle in pharmaceutically acceptable quantities. Accordingly, the present invention provides for (1) controlled and efficient delivery of these reactive materials to dentinal surfaces; (2) ease of storage; and (3) quick, efficient no-blockage dispensing.

Effective plasticizers include mono-, di- or tri- glycerides having a melting point from about 45° C. to about 70° C. and which can be readily melt blended with the PVA to provide the desired encapsulating agent with or without the use of a solvent. As used herein, "glyceride" refers to esters of glycerol and fatty acids in which one or more of the hydroxyl groups of glycerol are replaced with acid radicals. A preferred plasticizer is, for example, glyceryl monostearate. Although not wishing to be bound by a particular theory, it appears that the glyceride component contributes to the flexibility and elasticity of the PVA, which as a blend, forms a film on the first and second reactive materials, thus rendering the blend highly effective in its role as an encapsulant.

Other methods may be utilized for the manufacture of, for example, encapsulated first and second reactive materials such as spray congealing methods which are well known in the art. These methods include melting and blending the PVA/plasticizer; dispersing the first and second reactive materials at high shear; and atomizing the resultant dispersion or mixture into fine droplets which solidify when they contact the cooler atmosphere. These droplets are then dispersed within or on the surface of an appropriate delivery vehicle for administration of the unreacted strontium and fluoride sources to a dentinal surface.

In another embodiment of the present invention, there is provided a system for simultaneously administrating to targeted areas protected precursors which react to form a DHA agent. This system includes a base and a matrix which is in intimate contact with the base.

As used herein, the base is any bio-compatible material which can deliver first and second ionic precursors, such as for example, strontium- and fluoride- containing compounds to the oral cavity, and more particularly to a dentinal surface therein. Examples of suitable base materials include dissolvable tablets, confections, troches, chewing gums, toothpaste formulations and comestibles, including mouthwashes. As described hereinabove, comestibles include any compatible beverage or foodstuff which is retained in the oral cavity sufficiently long to release the active ingredients. In each of these, the first and second ionic precursors are released from the base in the course of chewing, sucking, brushing or imbibing and are allowed to pass over the dentin surfaces. As described in further detail hereinabove, when the base material is introduced into the oral cavity, changes in pH and temperature can also cause release of the ionic precursors from their protective bodies.

As described previously, the protective matrix of the present invention is in intimate contact with the base. Thus, the protective matrix, which contains the incorporated unreacted first and second ionic precursors, may be disposed upon the surface of the base, such as for example, as a film upon the surface of a gum. Alternatively, the protective matrix may be dispersed throughout the base material, such as for example, as discrete capsules in a toothpaste, mouthwash or lozenge. The form of the base and the physical disposition between the base and the matrix will vary depending upon the desired end product.

The protective matrix of the present invention includes protective bodies which incorporate by, for example, encapsulating, first and second ionic precursors of pharmaceutically acceptable strontium- and fluoride- containing compounds as described hereinabove. These protective bodies form, for example, a capsule around the first and second ionic precursors and are made of any material which will prevent reaction between, e.g., the fluoride and strontium ions of the two ionic precursors until they are delivered to the oral cavity, and in particular to the dentinal surfaces therein. These protective bodies must be bio-compatible and may include for example, cellulose, cellulose derivatives, starches, carbohydrates, gums, polyolefins, polyesters, waxes, polymers, proteins, gelatin, zein, and mixtures thereof.

The composition of the protective matrix of the present embodiment has been described hereinabove. Preferably, the protective matrix is a high molecular weight polyvinyl acetate. Similarly, the protective matrix of the present embodiment contains a plasticizer as described hereinabove.

An optional outer coating may be applied to the protective matrix incorporated first and second ionic precursors for added protection against premature mechanical or chemical break down thereof. The outer coating is a hydrophilic material and is preferably a hydrocolloid. The hydrocolloid may include for example, gum arabic, gelatin, carrageenan, polyvinylpyrrolidone, cellulose methyl cellulose, ethyl cellulose, hydroxyethyl cellulose, hydroxypropyl cellulose carboxymethyl cellulose and mixtures thereof.

The outer coating may be applied in an amount ranging from about 5.0% to about 50% by weight of the protective body, and preferably from about 15% to about 50% by weight. The application of the outer coating to the outer surface of the protective body may be accomplished by a variety of methods known in the art. Such methods include, for example, spray drying and fluidized bed coating.

EXAMPLE 1

Preparation of an Encapsulated Source of Strontium

An encapsulated source of strontium is prepared by melt blending 50 gm of polyvinyl acetate and 100 gm of glyceryl monostearate at a temperature of about 85 ° C. for about five minutes in a mixer. After removing the melt blend from the heat, 40 gm of strontium chloride is added and blended into the molten mass for an additional 5 minutes. The resulting semi-sold mass is chilled to 0° C. until a solid forms. The resulting solid is ground until the resulting encapsulant can pass through a 30 mesh sieve.

EXAMPLE 2

Preparation of an Encapsulated Source of Fluoride

The procedure as described in Example 1 is repeated to form an encapsulated source of fluoride by substituting 40 gm of sodium monofluorophosphate for the strontium chloride of Example 1.

EXAMPLE 3

Preparation of a Gum Delivery Vehicle for Encapsulated Strontium and Fluoride Sources Using the encapsulated sources of strontium and fluoride in Examples 1 and 2, a chewing gum delivery system is prepared by adding into a mixer 69.1 gm sugar, 1.0 gm encapsulated strontium from Example 1 and 1.0 gm encapsulated fluoride from Example 2 under mechanical stirring and heat for five minutes. To this mixer is added 26.4 gm of a molten gum base and 1.3 gm of a softener, such as for example, triacetin, previously melted at 95° C. The components are mixed for three minutes. The resulting gum product is rolled and scored.

Although illustrative embodiments of the present invention have been described herein, it is to be understood that the invention is not limited to those precise embodiments, and that various other changes and modifications may be effected therein by one skilled in the art without departing from the scope or spirit of the invention.

What is claimed is:

1. A delivery system for controlling the delivery of reactive ionic species to dentin hypgrsensitive areas comprising:

a polymeric bio-comrpatible delivery vehicle comprising unreacted, reactive ionic species of strontium and fluoride dispersed therein, said unreactcd ionic strontium and fluoride species being separately incorporated within polymeric protective matrices and forming a dentin-hypersensitivity-ameliorating composition when reacted, and said matrices preventing the premature reaction thereof until delivery of said ionic species to said dentin hyperscnsitive areas whereupon they react to form a precipitate.

2. The delivery system of claim 1, wherein said delivery vehicle is selected from the group consisting of dissolvable tablets, confections, troches, chewing gums, toothpaste formulations, and comestibles.

3. The delivery system of claim 1, wherein said unreacted, reactive ionic species of fluoride is a pharmaceutically acceptable fluoride-containing compound selected from the group consisting of sodium fluoride, sodium monofluorophosphate, potassium fluoride, lithium fluoride, zinc fluoride, ammonium fluoride, rubidium fluoride, potassium bifluoride, ammonium bifluoride, sodium silicofluoride and mixtures thereof.

4. The delivery system of claim 1, wherein said unreacted, reactive ionic species of strontium is a pharmaceutically acceptable strontium-containing compound selected from the group consisting of strontium chloride, strontium nitrate, strontium acetate, strontium bromide, strontium iodide, strontium broniate, strontium perchlorate, strontium formate, strontium lactate and mixtures thereof.

5. The delivery system of claim 1, wherein said protective matrices are bio-compatible materials selected from the group consisting of cellulose, cellulose derivatives, starches, carbohydrates, gums, polyolefins, polyesters, waxes, proteins, gelatin, zein, and mixtures thereof.

6. The delivery system of claim 1, wherein said unreacted, reactive ionic species of fluoride is sodium monofluorophosphate and said unreacted, reactive ionic species of strontium is strontium chloride.

7. The delivery system of claim 1, wherein said targeted areas are dentinal surfaces.

8. The delivery system of claim 1, wherein said dentin-hypersensitivity-ameliorating composition is formed at a dentinal surface when said unreacted, reactive strontium and fluoride materials are released from said protective matrices in response to a stimulus.

9. The delivery system of claim 8, wherein said stimulus is selected from the group consisting of chewing, sucking, brushing, imbibing, pH change, temperature change and mixtures thereof.

10. The delivery system of claim 1, wherein said unreacted, reactive materials are incorporated into said protective matrices by encapsulation.

11. A system for simultaneously administrating to a dentin hypersensitive area encapsulated precursors which react to form a dentin-hypersensitivity-ameliorating agent comprising;
   a) a base; and
   b) a polymeric matrix in intimate contact with said base comprising;
      i) a polymeric protective body separately encapsulating a first ionic precursor of a pharmaceutically acceptable source of strontium compounds;
      ii) a polymeric protective body separately encapsulating a second ionic precursor of a pharmaceutically acceptable source of fluoride compounds, wherein said protective bodies maintain said first and second ionic precursors in an unreacted state until delivery to said targeted area; and
      iii) a plasticizer.

12. The system of claim 11, wherein said base is selected from the group consisting of dissolvable tablets, confections, troches, chewing gums, toothpaste formulations, and comestibles.

13. The system of claim 11, wherein said at least first ionic precursor is a pharmaceutically acceptable fluoride-containing compound selected from the group consisting of sodium fluoride, sodium monofluorophosphate, potassium fluoride, lithium fluoride, zinc fluoride, ammonium fluoride, rubidium fluoride, potassium bifluoride, ammonium bifluoride, sodium silicofluoride and mixtures thereof.

14. The system of claim 11, wherein said at least second ionic precursor is a pharmaceutically acceptable strontium-containing compound selected from the group consisting of strontium chloride, strontium nitrate, strontium acetate, strontium bromide, strontium iodide, strontium bromate, strontium perchlorate, strontium formate, strontium lactate and mixtures thereof.

15. The system of claim 11, wherein said protective bodies are bio-compatible materials selected from the group consisting of cellulose, cellulose derivatives, starches, carbohydrates, gums, polyolefins, polyesters, waxes, proteins, gelatin, zein, and mixtures thereof.

16. The system of claim 11, wherein said at least first ionic precursor is sodium monofluorophosphate and said at least second ionic precursor is strontium chloride.

17. The system of claim 11, wherein said targeted area is a dentinal surface.

18. The system of claim 11, wherein said dentin-hypersensitivity-ameliorating agent is formed at a dentinal surface when said at least first and second ionic precursors are released from said protective bodies in response to a stimulus.

19. The system of claim 18, wherein said stimulus is selected from the group consisting of chewing, sucking, brushing, imbibing, pH change, temperature change and mixtures thereof.

20. The system of claim 11, wherein an optional outer coating is applied to said protective bodies of said at least first and second ionic species, respectively.

21. The system of claim 20, wherein said optional outer coating is selected from the group consisting of gum arabic, gelatin, carrageenan, polyvinylpyrrolidone, cellulose methyl cellulose, ethyl cellulose, hydroxyethyl cellulose, hydroxypropyl cellulose carboxymethyl cellulose and mixtures thereof.

22. The system of claim 11, wherein said protective body is an encapsulant.

23. A method of making a delivery system for amelioration of dentin hypersensitivity comprising:
   a) preparing a dentin-hypersensitivity-ameliorating-agent delivery system wherein two reactive ionic species comprising strontium and fluoride are chemically isolated, one from the other, by separately encapsulating each through the process comprising:
      i) entrapping a first ionic species comprising strontium in a mixture of polyvinyl acetate by melting and blending said first ionic species with said polyvinyl acetate and a plasticizer to form a chemically discrete domain containing said first reactive ionic species, cooling said mixture at ambient temperature while continuing to mix;
      ii) grinding said mixture to a desired particle size;
      iii) optionally coating said particles with a hydrophilic polymer material;
      iv) repeating steps i–iii with a second ionic species comprising fluoride replacing said first ionic species;
      vi) combining said encapsulated first and second ionic species in controlled, pharmaceutically acceptable quantities to form said delivery system;
   b) combining the resultant delivery system with a bio-compatible base for targeted delivery to said dentin.

* * * * *

UNITED STATES PATENT AND TRADEMARK OFFICE
CERTIFICATE OF CORRECTION

PATENT NO. : 5,792,446
DATED : August 11, 1998
INVENTOR(S) : Ashley, Robert A.

It is certified that error appears in the above-identified patent and that said Letters Patent is hereby corrected as shown below:

IN THE CLAIMS:

| | |
|---|---|
| Column 8, Line 26, | now reads "dentin hypgrsensitive", should read --dentin hypersensitive--; |
| Column 8, Line 28, | now reads "bio-comrpatible", should read --bio-compatible--"; |
| Column 8, Line 30, | now reads "said unreactcd ionic", should read --said unreacted ionic--; |
| Column 8, Line 37, | now reads "dentin hyperscnsitive", should read --dentin hypersensitive--. |

Signed and Sealed this

Eighth Day of December, 1998

*Attest:*

BRUCE LEHMAN

*Attesting Officer*   *Commissioner of Patents and Trademarks*